United States Patent [19]
Litz et al.

[11] Patent Number: 5,174,655
[45] Date of Patent: Dec. 29, 1992

[54] CALORIMETER SENSOR

[75] Inventors: Wilfried Litz; Adolf Schmidt; Ulrich Pallaske, all of Cologne; Reinold Rose, Leverkusen, all of Fed. Rep. of Germany

[73] Assignee: Bayer Aktiengesellschaft, Leverkusen, Fed. Rep. of Germany

[21] Appl. No.: 781,057

[22] Filed: Oct. 18, 1991

[30] Foreign Application Priority Data

Oct. 26, 1990 [DE] Fed. Rep. of Germany ....... 4034115

[51] Int. Cl.⁵ .................... G01K 17/00; G05D 23/19
[52] U.S. Cl. ....................................... 374/31; 436/147
[58] Field of Search ........................... 374/31, 34, 35; 364/556; 422/67; 436/147

[56] References Cited

U.S. PATENT DOCUMENTS

| | | | |
|---|---|---|---|
| 1,247,998 | 11/1917 | Parr | 374/34 |
| 4,456,389 | 6/1984 | Regenass et al. | 374/31 |
| 4,963,499 | 10/1990 | Stockton et al. | 374/31 X |

FOREIGN PATENT DOCUMENTS 3049105 12/1950 Fed. Rep. of Germany.

OTHER PUBLICATIONS

Dynamic Thermal Analyzer for Monitoring Batch Process, R. S. H. Wu; CEP Sep. 1989; pp. 57-61, (Rohm & Haas Co., Bristol, Pa.).

*Primary Examiner*—Daniel M. Yasich
*Attorney, Agent, or Firm*—Sprung Horn Kramer & Woods

[57] ABSTRACT

The invention relates to a process and an apparatus for determining the heat output rate in a reactor. This is achieved by determining the heat output rate in a sensor connected to the chemical reactor and taking into account the volume or mass ratio between the reactor and sensor contents. The apparatus allows balancing of the sensor, on the one hand, and continuous adjustment of the material composition and temperature of the reactor and sensor contents, on the other hand.

7 Claims, 7 Drawing Sheets

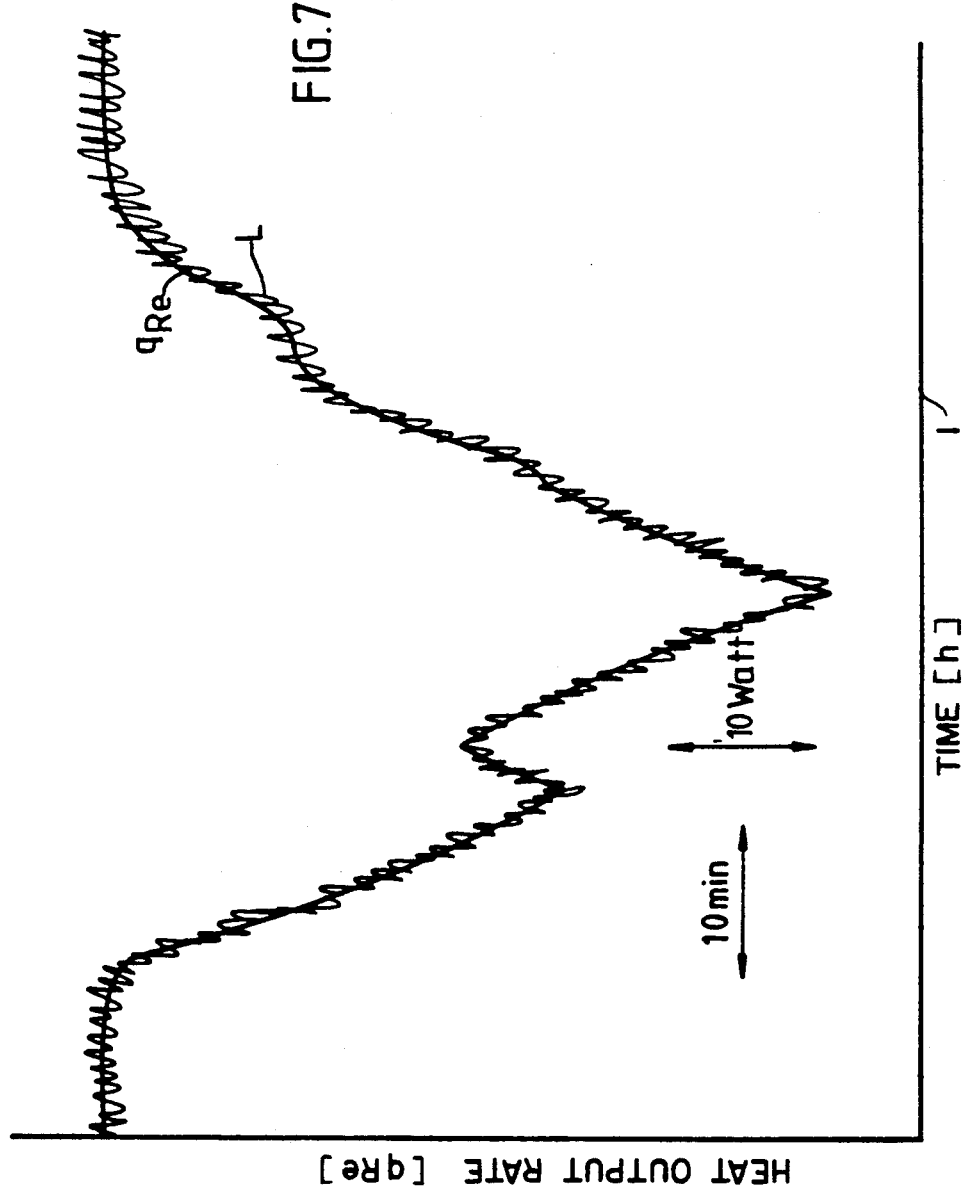

CALORIMETER SENSOR

BACKGROUND OF THE INVENTION

The invention relates to a process for measuring the heat output rate in a chemical reactor with the aid of a calorimeter, which comprises a measuring cell, an intermediate thermostat and a base thermostat, and taking as a basis the heat balance equation of the measuring cell as well as the heat balance equation of the intermediate thermostat.

The invention further relates to a calorimeter for effecting the process described above, comprising a measuring cell, which has at least one temperature detector, a controllable heating device with an output measuring circuit and an agitator, an intermediate thermostat, which has at least one temperature detector and a controllable heating device with an output measuring circuit, and a base thermostat, with the controllable heating device maintaining a constant temperature difference $\Delta T_1$ between the base and the intermediate thermostat.

The technical field of the invention is, in its broadest sense, process instrumentation and control (process I & C). Control of large production reactors by modern methods is frequently effected by so-called model-assisted process management. Here, from a system of state variables (temperature, pressure, concentrations etc.), the unknown state variables are determined by determining the remaining variables and by applying mathematical methods, such as the Kalman filter or the Luenberger observer. The measured variable which may be made most readily available to said model-assisted measuring process in chemical processes is temperature. Other state variables, such as pressure, concentrations etc., are often only measurable with difficulty or their recording involves considerable time delays. A further measured variable which is analytically very meaningful is the rate of the change of enthalpy (heat output rate) of a chemical process, since each chemical elementary reaction is linked with a change of enthalpy of a greater or lesser magnitude.

The difficulties involved in measuring the heat output rate in a production reactor, i.e. a reactor which in the main may have a capacity ranging from around 100 liters up to several cubic meters, are considerable. Such a system is difficult to isolate from environmental influences. It is known that the temperature in such a production reactor is always fluctuating to some extent, that the input into the reaction mass of agitator output by any agitators and the heat losses are difficult to determine precisely.

Also, the effective heat capacity of the reactor content normally changes continuously in the course of reaction and the diathermancy of the reactor walls is similarly influenced by the addition of reaction mass, so-called "fouling".

Because of these difficulties, calorimetric variables are frequently measured using trial reactors having a capacity of between 0.1 and 15 liters, whose heat balance is easier to control. Translation of the variables thereby obtained to production reactors of the above-mentioned capacity is, however, always fraught with uncertainties owing to the changed volume-to-surface ratio and the impossibility of keeping to process management variables in a large-scale reactor. There is therefore a need to determine the state variables as far as possible in the production reactor itself, i.e. on line.

Such a process is described, for example, in Chem. Eng. Progress 81,9 (1985), page 57/61. This known process is based on the mass or heat balance equations of the actual production reactor and of its surrounding jacket through which coolant is circulated. Besides taking an incomplete heat balance equation as a basis, the known process also has the drawback that only a rough account is taken of any change in the effective heat capacity and in the density of the reactor content.

SUMMARY OF THE INVENTION

The principal object of the present invention is therefore to develop an improved process for determining the heat output rate in a reactor.

This object is achieved in that the composition of the substance in the measuring cell of the calorimeter is continuously adjusted to the composition of the substance in the reactor ($q_{Mi}=0$ and $c_2=c_3$) and the temperature of the substance in the measuring cell is continuously adjusted to the temperature of the substance in the reactor ($m \cdot c_3 \cdot T_3 - m \cdot c_2 \cdot T_2)=0$ and the transport of substance from the reactor into the measuring cell is interrupted for a period $\delta t$ in order to determine the effective heat capacity of the measuring cell content $C_2$, taking as a basis the then prevailing heat balance $C_2 \cdot dT_2/dt = q_{Re} + q_{Rü2} - KF_{21} \cdot (T_2 - T_1)$, and, after determining the heat output rate $q_{Re}$ in the measuring cell, the heat output rate of the reactor is determined taking into account the volume or mass ratio between reactor and measuring cell contents.

The main advantage of the new process is that the heat output rate is measured parallel to the operating state of the production reactor but spatially separated from the latter in a measuring cell which may be balanced more easily and calorifically more precisely. Determination of the heat output rate is all the more precise, the more closely the composition of the measuring cell content and its temperature are adjusted to the conditions of the production reactor.

A further advantage of the new process lies in the determination of the effective heat capacity $C_2$ of the measuring cell content which, in most cases, because of the chemical reaction is subject to constant change.

A preferred variant of the new process is characterised in that, to determine the effective heat capacity $C_2$ of the measuring cell content, the temperatures $T_2$ and $T_1$ are measured in the period $\delta t$, $C_2$ and $KF_{21}$ are assumed to be constant therein, and $q_{Re}+q_{Rü2}$ for the period $\delta t$ are replaced by a mean heat output rate $q_m$.

This new process according to the invention has the advantage of simplifying evaluation of the chemical process. This applies particularly in cases where the activation energy of the reactions is known.

A further preferred variant of the new process is characterised in that, to determine the effective heat capacity $C_2$, the unknown parameters $C_2$ and $q_{Re}$ in the heat balance taken as a basis $$C_2 \cdot dT_2/dt = q_{Re} + q_{Rü2} - KF_{21} \cdot (T_2 - T_1)$$

are determined by measuring $T_2$ and $T_1$ during the period $\delta t$ and by applying known mathematical methods.

The advantage of this variant of the process is that the effective heat capacity and the heat output rate may be simultaneously determined in the measuring cell, without requiring an exact knowledge of the reaction in progress. After determining $KF_{21}$ and $q_{Rü2}$, as described below, and measuring $T_2$ and $T_1$, only $C_2$ and $q_{Re}$ are not accessible to direct measurement. The two variables are determined computationally by parameter matching ("fitting") to the measured temperature characteristic. Known methods such as, for example, the Kalman-Bucy filter are used for this purpose.

If the variable $dT_2/dt$ is determined by numerical differentiation, then a linear regression is also applicable.

A particularly preferred variant of the new process is characterised in that the temperature of the substance mixture upon entry into the measuring cell is kept equal to the temperature of the substance mixture in the reactor by heating—or cooling—the connection line between reactor and measuring cell.

The advantage of said variant is that any heat lost or absorbed by the substance mixture may more easily be compensated in the lines from the reactor to the measuring cell. Since disruptions in the energy content of the substance mixture, such as are caused for example by pumping or by the transfer of heat through the line wall, are difficult to measure, it has proved advantageous to compensate said disruptions in the supply lines themselves. This avoids having to include further terms in the heat balance equation of the measuring cell.

The calorimeter for effecting the new process is a further development of the reactor calorimeter known from German Offenlegungsschrift DE-30 49 105-A1. The latter is a closed system. The known calorimeter may only be operated batch-wise under isothermal conditions. It is therefore only possible to determine the heat output rate of a reaction mixture introduced at the start of reaction at a constant temperature during the course of reaction.

The new calorimeter is characterised in that it has at least one connection for transporting substance from the reactor into the measuring cell of the calorimeter, and a measuring and control circuit which adjusts the temperature in the measuring cell to the temperature in the reactor.

Only by continuously adjusting the substance composition and the temperature can the calorimeter be used as an on-line sensor for the heat output rate in a large-scale reactor.

A particularly preferred variant of the new calorimeter is characterised in that the calorimeter has a connection with a pump device for circulating substance between the reactor and the measuring cell.

So long as the volume of the measuring cell is small compared to the capacity of the production reactor and hence the material loss may be kept within commercially acceptable limits, it is also feasible to operate the sensor without feedback of the substance mixture into the reactor. The preferred variant does however have the advantage that there is no loss of material. However, so that the influence of the initial content of the measuring cell upon the reactor remains negligible and the calorimeter may still be isolated relatively easily from the environment, it is advantageous to set an upper limit on the size of the measuring cell even with circulation of material. Thus, the quantity of substance in the measuring cell should be at most 1/10 of the quantity of substance in the reactor. However, to prevent adulteration of the reactor content, a quantity ratio of less than 1:100 is to be preferred. Taking conventional production reactors as a scale, this means that the volume of the measuring cell is below 10 l, but preferably below 1.5 l. The lower limit for the volume of the measuring cell is dictated by the level of the heat output rate and by how necessary it is still to determine said rate in a clearly distinct manner from possible disturbing influences. Given the usual heat output rates for polymer reactions, measurement with a measuring cell volume of more than 10 $cm^3$ is feasible. However, to achieve improved measuring accuracy, the volume of the measuring cell is preferably more than 100 $cm^3$.

A further preferred embodiment of the new apparatus is characterised in that the entry point of the connection into the measuring cell has a temperature detector and the connection has a controllable heating device with a control unit, which adjust the inlet temperature of the substance mixture coming from the reactor into the measuring cell to the temperature prevailing in the reactor. The effect achieved by equipping the connecting section from the reactor to the measuring cell with a controllable heating/cooling device is that the substance mixture, on entry into the measuring cell, is at the same temperature as it is in the reactor. Thus, measurement of the heat output rate is not adulterated by the pump output of the pumping device and/or by the heat loss through the line walls.

The new process and the calorimeter are described in greater detail hereinafter with reference to the drawings.

BRIEF DESCRIPTION OF THE DRAWINGS

FIG. 7 reproduces the characteristic of the heat output rate $q_{Re}$ simulated in the test system and of the measured total output L at a constant reactor temperature $T_3$.

DESCRIPTION OF THE PREFERRED EMBODIMENTS

Figure 1:
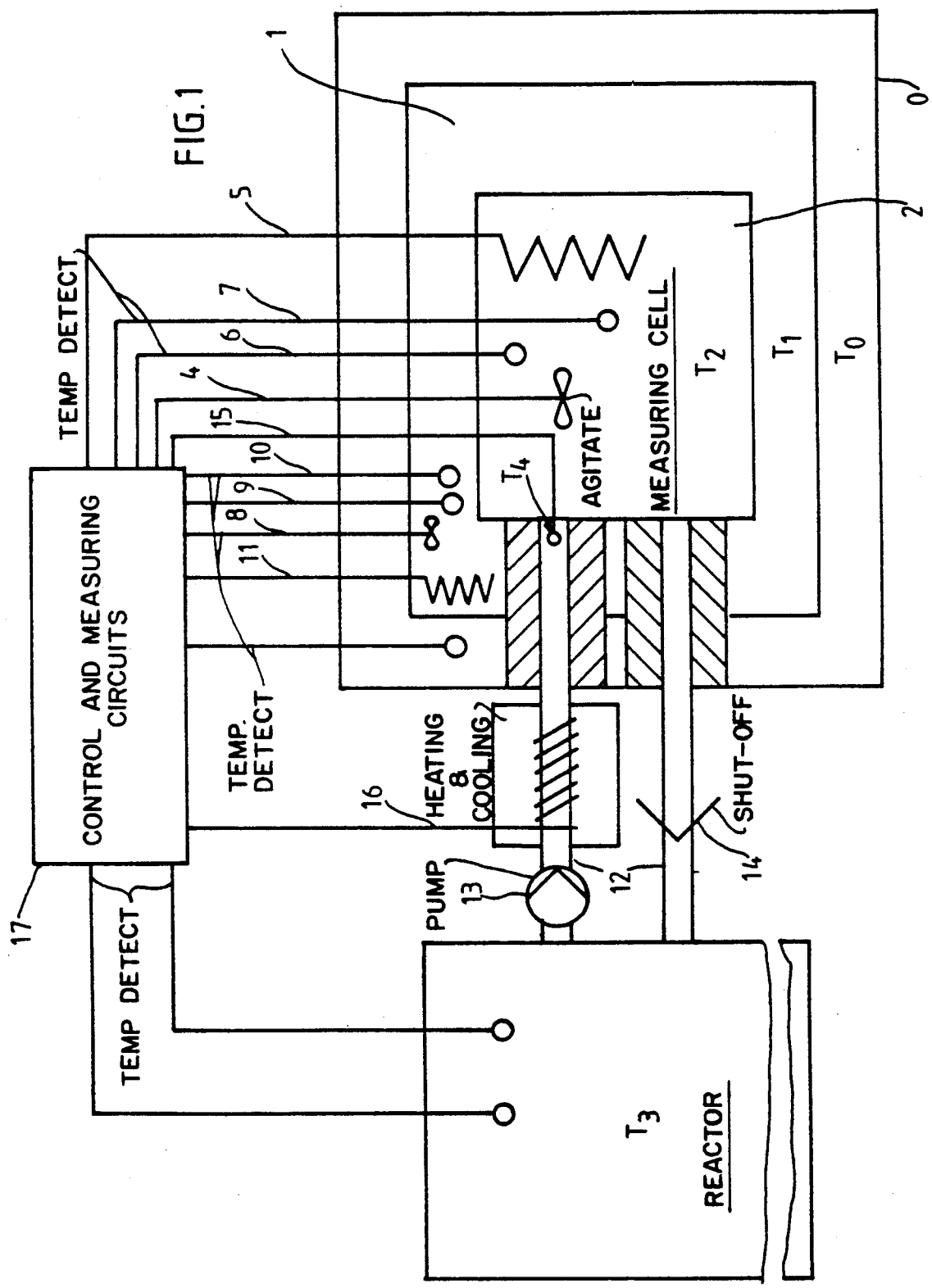
FIG. 1 shows the diagram of the calorimeter sensor connected to a chemical reactor.

The sensor comprises a measuring cell 2 situated in a thermal environment or thermostat (intermediate thermostat) 1, which is in turn surrounded by a base thermostat 0. The measuring cell 2 is equipped with agitator 4, power breakers, a controlled electric heating element 5 and two temperature detectors 6, 7. The intermediate thermostat 1 is likewise equipped with an agitator 8, two temperature detectors 9, 10 and a heating element 11. The sensor further has two lines 12 for transporting substance between measuring cell 2 and a production reactor 3. Associated with the line 12 are a pump device 13, a controllable shut-off device 14, a temperature detector 15 and a heating device 16. The control and regulating lines converge in a conventionally control and measuring element 1 which acts to control the heating devices 5, 11 and 16 in dependence upon the temperatures sensed by the detectors 6, 7, 9, 10 and 15.

The measuring cell 2 is ideally thoroughly mixed. The bypass flow of the production reactor 3 circulates through it.

The temperatures prevailing in the various elements of the calorimeter sensor are designated as follows:

The temperature of the base thermostat 0 is designated $T_0$, the temperature of the intermediate thermostat 1 is designated $T_1$ and the temperature of the measuring cell 2 is designated $T_2$. Furthermore, the temperature of the reactor 3 is designated $T_3$ and the temperature at the outlet of the supply line 12 from the reactor 3 into the measuring cell 2 is designated $T_4$. The temperature $T_3$ of the reactor 3 is predetermined by external circumstances and the temperature $T_0$ of the base thermostat 0 is appropriately selected and held constant by control unit 17.

The control unit maintains a temperature gradient between the thermostats of the sensor ($T_0 < T_1 < T_2 = T_3 = T_4$). As a result of the duplicate design of the temperature detectors, not only the absolute values but also the relevant temperature differences may easily be determined.

For the measuring cell 2, the heat balance is generally $$C_2 \cdot dT_2/dt = q_{Re} + q_{Mi} + q_{R\ddot{u}2} + L_2 + m \cdot c_3 \cdot T_3 - m \cdot c_2 \cdot T_2 - KF_{21} \cdot (T_2 - T_1)$$

in which $C_2$ = effective heat capacity of the measuring cell content,
$q_{Re}$ = heat output rate as a result of reaction in the measuring cell,
$q_{Mi}$ = heat output rate as a result of mixing in the measuring cell,
$q_{R\ddot{u}2}$ = heat output rate as a result of agitation in the measuring cell,
$L_2$ = electrical heat output in the measuring cell,
m = mass flow through the measuring cell,
$C_3$ = specific heat of the inflow mass (production reactor),
$C_2$ = specific heat of the outflow mass (measuring cell),
$T_3$ = temperature of the production reactor,
$T_2$ = temperature of the measuring cell,
$T_1$ = temperature of the intermediate thermostat,
$KF_{21}$ = diathermancy of the measuring cell to the intermediate thermostat.

As a result of the constantly controlled heat output $L_1$ in the intermediate thermostat 1, a selected temperature difference $\Delta T_1 = T_1 - T_0$ is constantly maintained between base thermostat 0 and intermediate thermostat 1. The heat output $L_2$ in the measuring cell 2 is regulated in such a way that the temperature in the measuring cell 2 corresponds to the temperature in the production reactor 3: $T_2 = T_3$. The temperature difference between measuring cell 2 and intermediate thermostat 1 is therefore generally not constant:

$$T_2 - T_1 \equiv \Delta T_2(t)$$

After the start of regulation and adjustment of the control equilibrium, the temperature of the measuring cell 2 at that moment corresponds to the temperature of the production reactor 3, i.e. the following applies:

$$T_3 = T_2 = f(t) \text{ and } dT_3/dt = dT_2/dt \equiv g(t)$$

which is the rate of change of temperature in the measuring cell.

Consequently, the heat balance is simplified to $$C_2 \cdot g = q_{Re} + q_{Mi} + q_{R\ddot{u}2} + (c_3 - c_2) \cdot m \cdot f + L_2 - KF_{21} \cdot (f - T_1).$$

After adjustment of the quasi steady state, the composition of the reaction mass in the measuring cell 2 corresponds to that of the reactor 3. As a result, no more mixing heat arises ($q_{Mi} = 0$) and the difference of the specific heats $c_3$ and $c_2$ is zero.

This results in $$q_{Re}(t) = [C_2(t) \cdot g(t) + KF_{21}(t) \cdot (f(t) - T_1) - q_{R\ddot{u}2}(t)] - L_2(t) = L_b(t) - L_2(t)$$

The parenthetical expression $L_b(t)$ represents the heat output required to establish equality of measuring cell temperature $T_2$ and production reactor temperature $T_3$ when no heat output as a result of reaction occurs in the measuring cell ($q_{Re} = 0$). If f(t) is constant and hence g(t) equals zero, $L_b(t)$ may still vary, namely when the diathermancy $KF_{21}$ varies, e.g. as a result of a change in the viscosity of the reaction mass or caking of reaction mass onto the measuring cell wall. $L_b(t)$ must be known in order, upon occurrence of heat output ($q_{Re} \neq 0$), to be able to calculate the heat output rate $q_{Re}(t)$ from the recorded variable L(t). To determine $L_b(t)$, the following must be known:

the time characteristic of the temperature of the production reactor 3 and of the measuring cell 2: f(t),
the time characteristic of the rate of change of the temperature of the reactor 3 and of the measuring cell 2: g(t),
the time characteristic of the diathermancy from the measuring cell 2 to the intermediate thermostat 1: $KF_{21}(t)$,
agitator output in the measuring cell 2: $q_{R\ddot{u}2}(t)$, and
the time characteristic of the effective heat capacity of the measuring cell content: $C_2(t)$.

a) The time characteristic of the temperature f(t) in the measuring cell 2 is obtained by direct recording of the measuring cell and reactor temperature.

b) The time characteristic of the rate of change g(t) of the measuring cell temperature is obtained by on-line differentiation of f(t).

c) The time characteristic of the diathermancy $KF_{21}(t)$ is obtained with the aid of measured variables of the intermediate thermostat 1. In control equilibrium, the following heat balance applies for the intermediate thermostat 1:

$$KF_{21} \cdot (T_2 - T_1) + L_{R\ddot{u}1} + L_1 = KF_{10} \cdot (T_1 - T_0)$$

or $$KF_{21} = [KF_{10} \cdot (T_1 - T_0) - L_{R\ddot{u}1} - L_1]/(T_2 - T_1),$$

in which $KF_{21}$ = diathermancy from the measuring cell 2 to the intermediate thermostat 1, $KF_{10}$ = diathermancy from intermediate thermostat 1 to base thermostat 0, $L_{Rü1}$ = agitator output in the intermediate thermostat 1, $T_2$ = temperature in the measuring cell 2, $T_1$ = temperature in the intermediate thermostat 1, $T_0$ = temperature in the base thermostat 0, $L_1$ = heat output in the intermediate thermostat 1.

For continuous determination of $KF_{21}$, $KF_{10}$ and $L_{Rü1}$ must be known. When temperature is constant (and practically in the event of a not too great change in temperature), the diathermancy $KF_{10}$ (intermediate thermostat/base thermostat) is, for a given tempering liquid and a given filling ratio of the intermediate and base thermostats 1, 0 and a given number of revolutions of the agitator 8, a constant quantity. To some extent, it represents an apparatus constant which, when using the measuring system as a closed system, i.e. disconnected from the production reactor 3, may be determined as follows:

If $L_1(1)$ and $L_1(2)$ are two manually adjus constant heat outputs and $T_1(1)$ and $T_1(2)$ are the adjusting equilibrium temperatures, $KF_{10}$ arises from $$KF_{10} = [L_1(1) - L_1(2)] / [T_1(1) - T_1(2)].$$

When temperature is constant (and practically in the event of a not too great change in temperature), the agitator output $L_{Rü1}$ in the intermediate thermostat 1 is, like $KF_{10}$, for a given tempering liquid and a given filling ratio of the intermediate thermostat 1 as well as a given number of revolutions of the agitator 8, also to some extent an apparatus constant which may likewise be determined by using the measuring system as a closed system: before connecting the measuring cell 2 to the production reactor 3, with the aid of two manually adjusted heat outputs of the measuring cell 2 $L_2(1)$ and $L_2(2)$ and the adjusting equilibrium temperatures $T_2(1)$ and $T_2(2)$, the diathermancy (measuring cell/intermediate thermostat) $KF'_{21}$ (representative of the substance actually situated in the measuring cell 2) is determined from $$KF'_{21} = [L_2(1) - L_2(2)] / [T_2(1) - T_2(2)].$$

By means of $KF'_{21}$ and $KF_{10}$ the agitator output in the intermediate thermostat is then given by the heat balance $$L_{Rü1} = KF_{10} \cdot (T_1 - T_0) - KF_{21} \cdot (T_2 - T_1) - L_1.$$

d) The agitator output $q_{Rü2}$ may, when the agitator 4 is driven by an electric motor in which there is no armature reaction, be determined from the current consumption of the motor: the total torque D summoned up by an electric motor during agitation of a reaction mass is proportional to the current consumption I, with the proportionality factor d (torque per ampere) in conventional motors being a function of the current intensity $$D = d(I) \cdot I.$$

In an electric motor with no armature reaction, however, the proportionality factor (torque factor) is constant, so that $$D = \text{const} \cdot I = d \cdot I.$$

The total torque summoned up by the motor during agitation of the reaction mass is made up of the internal lost torque of the engine (eddy currents, friction in the motor bearings), the external lost torque in the agitator bearing system (both dependent on the angular velocity) and the useful torque:

$$D = D_{lost} + D_{useful}.$$

For the output of a motor without armature reaction the following therefore applies $$L_{Mo} = (D_{lost} + D_{useful}) \cdot w = D_{lost} \cdot w + q_{Rü2} = d \cdot I \cdot w,$$

in which w is the angular velocity of the motor shaft.

If care is taken to ensure that the losses in the agitator bearing system and the number of revolutions of the agitator 4 remain unchanged, i.e. that $D_{lost}$ remains constant, with said angular velocity (number of revolutions) the following applies $$q_{Rü2} = L_{Mo} - \text{const} = d \cdot w \cdot I - \text{const}.$$

The value of the constant is obtained by allowing the agitator 4 to operate at the selected number of revolutions without load (i.e. with the measuring cell 2 empty). Then, $q_{Rü2} = 0$ and $\text{const} = d \cdot w \cdot I_o$. At the selected number of revolutions and with measuring cell 2 full, the agitator output is therefore determined by $q_{Rü2} = d \cdot w \cdot (I - I_o)$.

e) Unlike f, g, $KF_{21}$ and $q_{Rü2}$, the time characteristic of the effective heat capacity $C_2$ cannot be calculated from continuously recordable measured data. Instead, the effective heat capacity $C_2$ is determined at intervals by means of an approximation relation.

Figure 3:
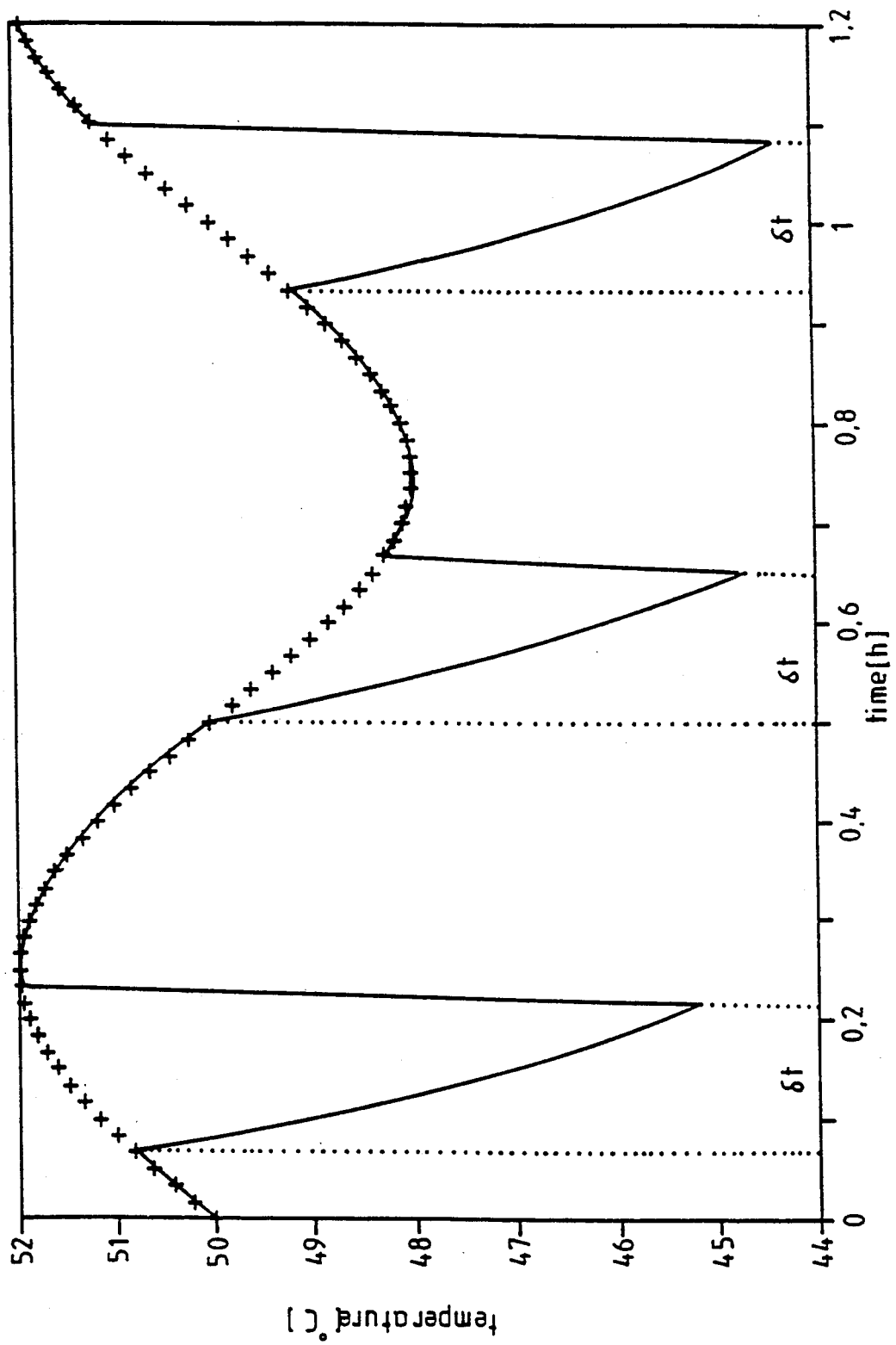
FIG. 3. shows the temperature characteristic for the reactor (+ — line) and the measuring cell of the sensor (continuous line) during the first hour of the reaction.

For said purpose, the measuring cell 2 is at various times $t_o$ disconnected from the production reactor 3 for a short period $\delta t$, and moreover the heat output $L_2$ is disconnected and the temperature characteristic $T_2$ is recorded. FIG. 3 shows the resulting thermal characteristic $T_3$ for the reactor and for the measuring cell $T_2$. In the periods of disconnection $\delta t$, the temperature $T_2$ drops. Under said conditions, the heat balance for the measuring cell (with $q = q_{Re} + q_{Rü2}$) is $$C_2 \cdot dT_2/dt = q - KF_{21} \cdot (T_2 - T_1)$$

or because $T_1 = \text{const}$ $$d(T_2 - T_1)/dt = q/C_2 - KF_{21} \cdot (T_2 - T_1)/C_2.$$

The heat output rate $q = q_{Re} + q_{Rü2}$, the effective heat capacity $C_2$ and the diathermancy $KF_{21}$ are functions of temperature and time. If the time constant of the reaction is high compared to the time constant of the temperature drop, the period $\delta t$ short and the temperature drop low, $C_2$, $KF_{21}$ and $q_{Rü2}$ in the period $\delta t$ may be assumed to be virtually constant and q may, in approximation using the Arrhenius relation, be replaced by a mean heat output rate $q_m$:

$$q_M \approx (q(t_o) - q_{ü2}) \cdot \exp(-E/RT_{2,m}) / \exp(-E/RT_2(t_o)) + q_{Rü2}.$$

Here, $q(t_o)$ = heat output rate at time $t_o$ of disconnection of the measuring cell, $q_{Rü2}$ = agitator output in the measuring cell at time $t_o$, $T_{2,m} = (T_2(t_o) - T_2(t_o + \delta t))/\ln (T_2(t_o)/T_2(t_o + \delta t))$ mean temperature in the measuring cell in period $\delta t$, E = activation energy of the reaction, R = gas constant.

Hence, in the period $\delta t$ the following approximately applies $$d(T_2 - T_1)/dt = q_m/C_{2,m} - KF_{21} \cdot (T_2 - T_1)/C_{2,m}.$$

From which $$[T_2(t) - T_1 - q_m/KF_{21}] = [T_2(t_o) - T_1 - q_m/KF_{21}] \cdot \exp(-KF_{21} \cdot t/C_{2,m}).$$

If $T_2(t) - T_1 - q_m/KF_{21} = a(t)$ is set, the effective heat capacity $C_2$ may therefore be determined by the relation:

$$C_{2,m} = (t_2 - t_1) \cdot KF_{21}/\ln (a(t_1)/a(t_2)),$$

in which $t_1$ and $t_2$ are two points of time within the period $\delta t$.

The difference between the value $C_{2,m}$ thus calculated and the true effective heat capacity $C_{2,w}$ is all the smaller, the greater the time constant of the reaction compared to the time constant of the temperature drop and the greater the heat flow from the measuring cell 2 into the intermediate thermostat 1 compared to the heat output rate.

Testing to establish whether the effective heat capacity may be determined sufficiently precisely, i.e. ultimately to determine the usefulness of the measuring system and its range of application, was carried out using simulation calculations. The basis of the simulation was a chemical reaction formally corresponding to a polymerisation with an induction phase:

| | |
|---|---|
| reaction scheme | A → A* → P |
| reaction rates | $r_1 = k_1 \cdot a$ |
| | $r_2 = k_2 \cdot a^*$ |
| Arrhenius law | $k_i = k_{oi}\exp(-E_i/RT)$ |
| pre-exponential factors | $k_{o1} = 6 \cdot 10^8 s^{-1}$ |
| | $k_{o2} = 2 \cdot 10^8 s^{-1}$ |
| activation energies | $E_1 = 77$ kJ/mol |
| | $E_2 = 77$ kJ/mol |
| reaction heat | |
| of first reaction stage | $\Delta H_1 = 0$ kJ/mol |
| of second reaction stage | $\Delta H_2 = -84$ kJ/mol |
| start concentrations | $a_o = 0.006$ mol/g |
| in the reactor | $a_o^* = 0$ mol/g |
| | $P_o = 0$ mol/g |
| start concentrations | $a_o = a_o^* = P_o = 0$ mol/g |
| in the measuring cell | or as in the reactor |
| flow rate through the measuring cell | m = 1.67 g/s |
| content of measuring cell 1 | $G_1 = 1000$ g |
| content of reactor | $G_3 >> G_1$ |
| diathermancy | $KF_{21} = 8$ W/K or variable |
| effective heat capacity | $C_{2,w} = 4,186$ J/K or variable |
| agitator output | $q_{Rü2} = 4$ W |
| set reactor temperature | $T_3 = 50°$ C. |
| temperature in intermediate thermostat | $T_1 = 40°$ C. |

Figure 2:
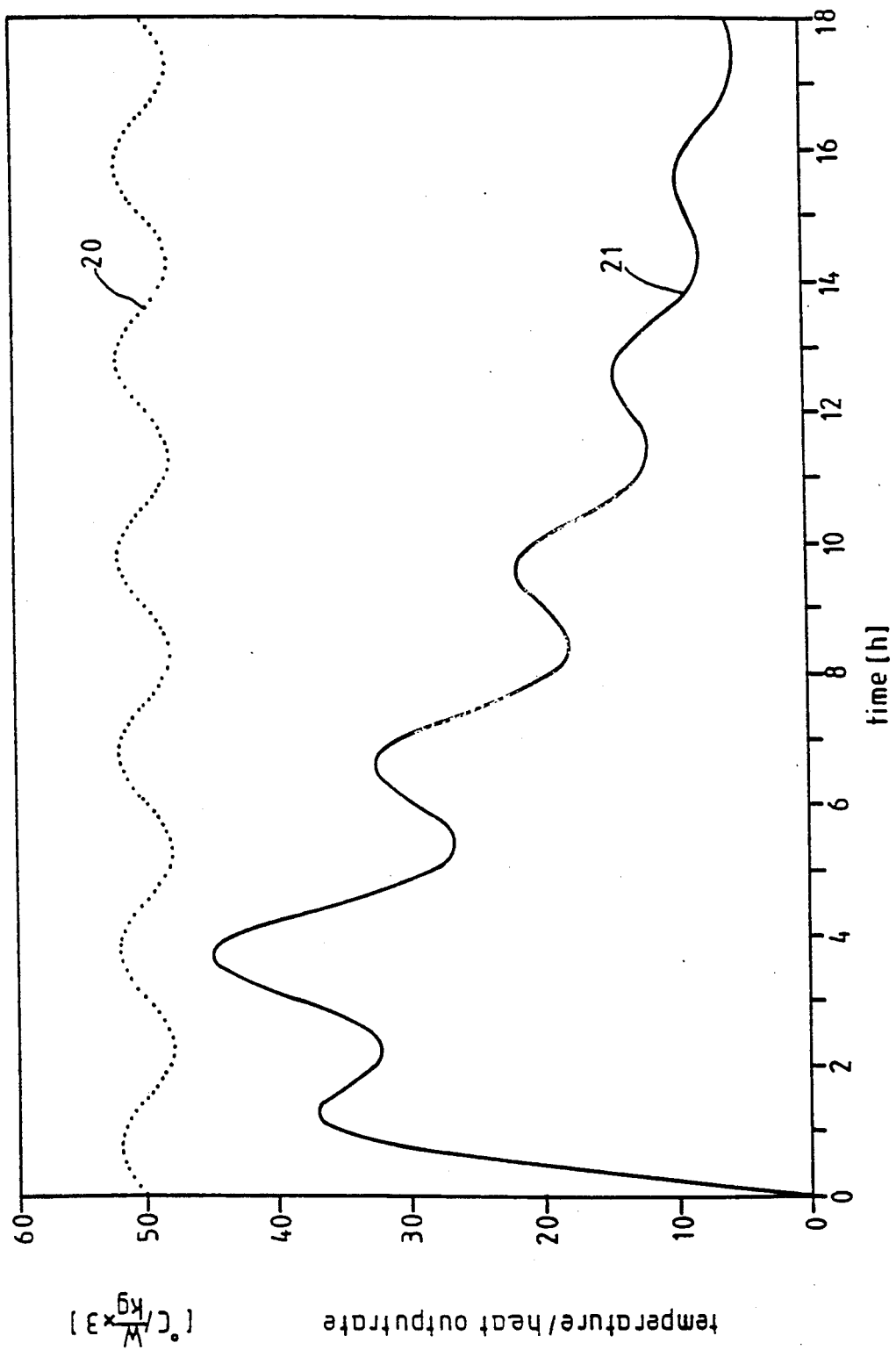
FIG. 2 shows the graph of the values presented for simulating the temperature fluctuations of the reactor (dotted line (20)) and the heat output rate of a reaction (21).

Without restricting the general nature, it was assumed that the reactor temperature $T_3$ fluctuates sinusoidally with the amplitude $\Delta T = 2°$ C. The period of oscillation was varied. FIG. 2 shows, for example, the time characteristic of the temperature for a period of oscillation of 3 hours as well as the corresponding specific heat output rate $q_{Re}$ (W/kg) in the reactor 3 for a period of oscillation of 3 hours. FIG. 3 reproduces the time characteristic of the temperature of reactor 3 and measuring cell 2 during the initial phase of the reaction. The measuring cell is in control equilibrium, i.e. the measuring cell and the reactor in their coupled state are at the same temperature. During the initial phase, they were disconnected three times and the effective heat capacity $C_2$ was calculated from the temperature decay curve of the measuring cell. The graph shows the decay curve of the measuring cell temperature $T_2$, as arose in the disconnection periods $\delta t$. The first $C_{2,m}$ value was determined from the temperature decay curve prior to reaction start ($q_{Re} = 0$). Said value was determined using the measurement of the temperature decay curve of the measuring cell 2 prior to reaction start.

It was additionally assumed that the activation energy E was not known. Without knowing the activation energy, no mean heat output rate $q_m$ may be calculated for the disconnection phase. In this case, it was therefore assumed that the heat output rate during the disconnection phase continues to be equal to that at the time $t_o$ of disconnection. $q_m = q(t_o)$ was therefore set.

However, since the reaction rate and hence the heat output rate as a result of reaction are in any case temperature-dependent, when the kinetics are unknown it is more advantageous to arrange a mean activation energy of 20 kcal/mol = 84 kJ/mol for a normal polymer reaction.

The following table shows the results of calculating the effective heat capacity $C_{2,m}$ of the measuring cell content at eight intervals spaced over the total reaction period (18 hours). In case (a), the activation energy E was known and it was possible to calculate $q_m$ using the method described above; in case (b), E is assumed to be unknown. $q_m$ cannot therefore be calculated and is replaced by $q(t_o)$. The disconnection period was in each case 10 minutes.

| Time [h] | (a) $C_{2,m}$[J/K] | (b) $C_{2,m}$[J/K] |
|---|---|---|
| 0.1 | 4120 | 3862 |
| 0.7 | 4124 | 3891 |
| 1.1 | 4128 | 3915 |
| 2.5 | 4156 | 3981 |
| 3.8 | 4178 | 4049 |
| 6.0 | 4178 | 4049 |
| 12.0 | 4185 | 4127 |
| 18.0 | 4188 | 4161 |

The actual value was $C_{2,w} = 4186$ J/K. The simulation demonstrated that the $C_2$ calculation produces accurate values throughout the reaction period, i.e. even with a decreasing heat output rate.

When taking the mean of 30 measured values, the following errors arose:

a) with the activation energy of the reaction known, i.e. with calculation of $q_m$, $C_{2,m} = C_{2,w} \cdot (1 \pm 6.3 \cdot 10^{-3})$ J/K, b) with the activation energy of the reaction unknown, i.e. assuming $q_m = q(t_o)$, $C_{2,m} = C_{2,w} \cdot (1 \pm 3.3 \cdot 10^{-2})$ J/K.

From the law of error propagation it follows that the mean error of the reference line $L_b$ is primarily characterised by the rate of change g of the reactor temperature $T_3 = T_2$. Under the test conditions taken as a basis, this produced at most in case a) $L_b = L_{b,w} \cdot (1 \pm 9.6 \cdot 10^{-4})$ W b) $L_b = L_{b,w} \cdot (1 \pm 4.8 \cdot 10^{-3})$ W This applied down to a ratio of 15:1 of the time constant of reaction and temperature drop.

Figure 4:
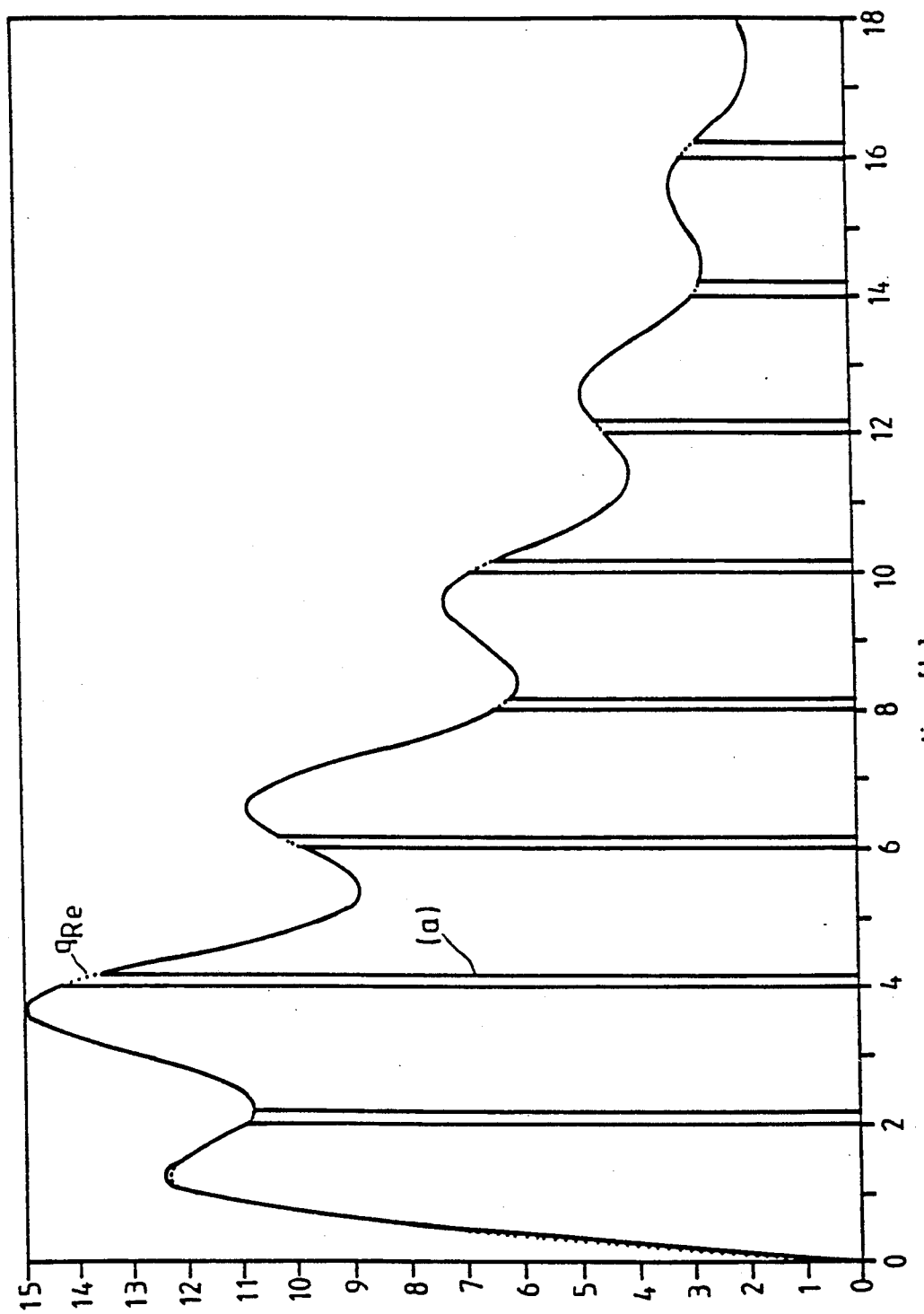
FIG. 4 illustrates the comparison between the preset heat output rate of the reactor ($q_{Re}$) and the heat output rate determined using the new process when the activation energy E of the reaction is known (a).
Figure 5:
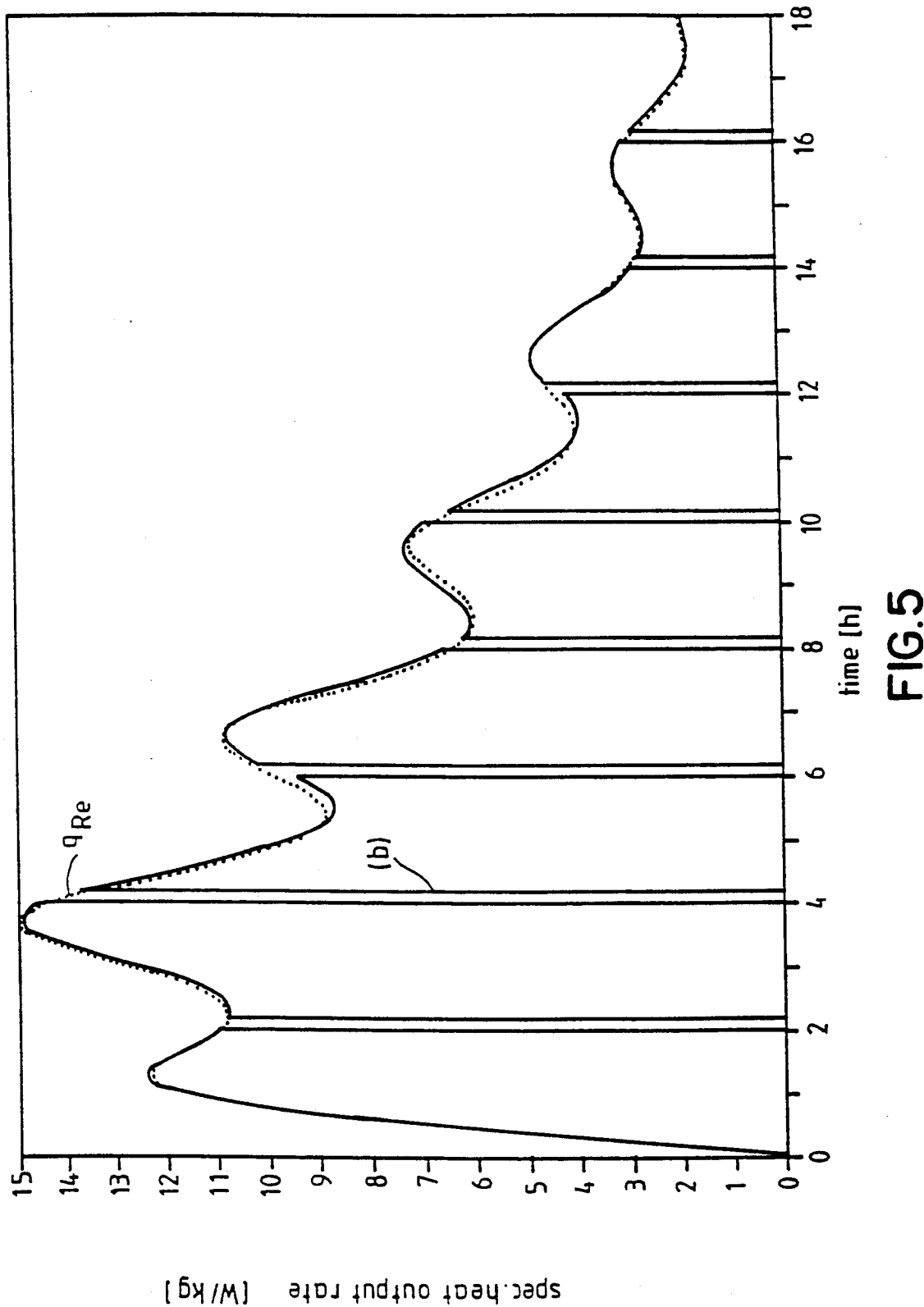
FIG. 5 illustrates the comparison between the preset heat output rate of the reactor ($q_{Re}$) and the heat output rate determined using the new process when the activation energy E of the reaction is unknown.

FIGS. 4 and 5 show the characteristic of the heat output rates determined using the new process and preset in the reactor. In FIG. 4, the activation energy E was used for calculation (case (a)) and, in FIG. 5, as described, $q_m$ was replaced by $q(t_o)$ (case (b)). The comparison shows that—although both variants of the process are very consistent with the setpoint selection—variant (a) is more accurate. The characteristic of the calculated curve for $q_{Re}$ is interrupted in the periods $\delta t$ during which the measurements of the temperature decay curves, which are required to determine the effective heat capacity $C_{2,m}$, were carried out.

The main precondition for meaningful use of the flow calorimeter is that, just as with any sensor which is intended to provide a representative indication of the general state of the reaction mixture in the production reactor, the content of the production boiler is thoroughly mixed.

In homogeneous or quasi-homogeneous reaction systems, in which the exchange of material does not have any influence in terms of reaction kinetics, it may be used without difficulty. The sole requirement is that the reaction mass must not be too viscous otherwise temperature striae will arise in the measuring cell and lead to control malfunctions. With heterogeneous reaction mixtures, in which the conversion rate may be co-determined by the material exchange between the phases, the specific agitator output in the measuring cell should be set in such a way that, in the measuring cell 2, the material permeability ($k_L a$ value) corresponds to that in the production reactor 3. This is easily possible on the basis of the known rules of transfer in agitation technology.

Since the actual heat output rate in a large-scale reactor—as mentioned above—may only be determined very imprecisely using conventional known methods, the process was carried out in a test system in which the heat output rate actually arising in the measuring cell 2 as a result of chemical reactions was replaced by defined electric heating. Besides the sensor, the test system also comprised a laboratory thermostat, which in a defined manner followed the temperature fluctuations of the production reactor 3, as well as the described auxiliary devices (lines, pumps, supply line tempering devices). The supply lines 12 to the measuring cell 2 were also provided with a temperature regulating device 17 which tempers the inflow mass to the measuring cell in such a way that its temperature $T_4$, despite changing slightly on the way towards the sensor (as a result of the pump output, radiation etc.), at the inlet into the measuring cell 2 is always the same as the temperature $T_3$ of the production reactor 3. The system was filled with an inert substance (silicone oil), so that no disruptive chemical reactions arose in the content. Because $q_{Re}=0$, the relation already described above $$q_{Re}=L_b-L_2=[C_2{}^*dT_2/dt+KF_{21}{}^*(T_2-T_1)--q_{Rü2}]-L_2$$

is simplified to:

$$L_2=L_b=C_2{}^*dT_2/dt+KF_{21}{}^*(T_2-T_1)-q_{Rü2}.$$

i.e. the calculated reference quantity $L_b$ must agree with the measured quantity $L_2$.

Figure 6:
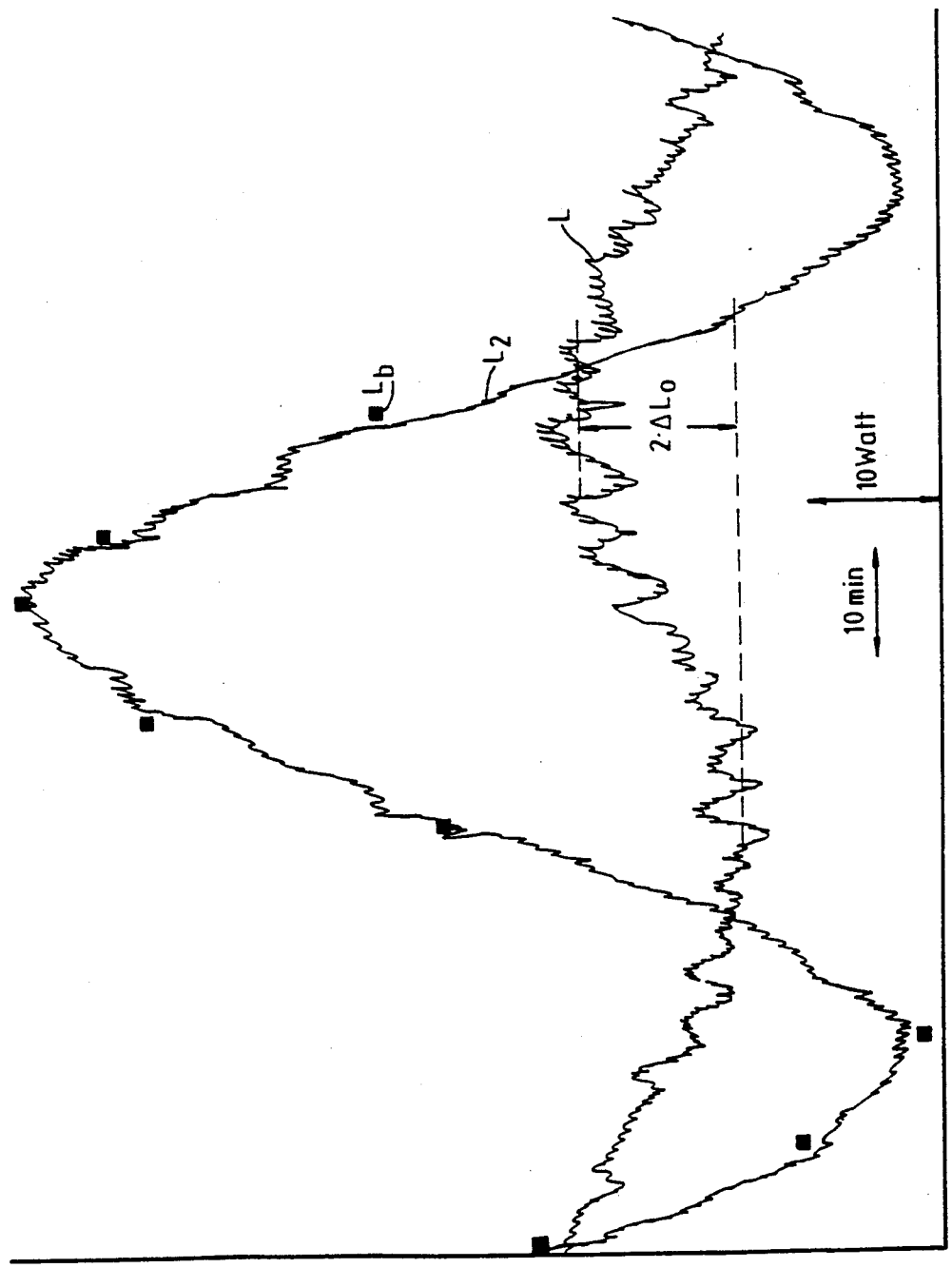
FIG. 6 illustrates the comparison of measured heat output $L_2$ in the measuring cell with the variable $L_b$ calculated on the basis of the valid heat balance equation, as well as the total output L of the sensor with the fluctuation amplitude $\Delta L_o$ of a test system.

FIG. 6 shows the characteristic of the measured and the calculated heat output ($L_2$ and $L_b$) in the event of sinusoidal fluctuation of the temperature of the production reactor $T_3$ by 2° C. The points $L_b$ were calculated using the relation $L_b=C_2{}^*dT_2/dt+KF_{21}{}^*(T_2-T_1)-q_{Rü2}$. They lie sufficiently accurately along the measured curve $L_2$.

As a result f combining the heat balances for the intermediate thermostat $T_1$ and the measuring cell $T_2$ in control equilibrium (see above) it further follows that $$\begin{aligned}q_{Re}&=[KF_{10}{}^*\Delta T_1-q_{Ru1}]-[L_1+L_2+q_{Ru2}]+C_2{}^*dT_2/dt\\&=[KF_{10}{}^*\Delta T_1-q_{Ru1}]-L+C_2{}^*dT_2/dt\end{aligned}$$

in which $KF_{10}$ and $\Delta T_1$ are respectively the diathermancy and temperature difference between intermediate thermostat and base thermostat, $q_{Rü1}$ is the agitator output in the intermediate thermostat, L is the sum of the thermal outputs $L_1$, $L_2$, $q_{Rü2}$.

Since $KF_{10}$, $\Delta T_1$ and $q_{Rü2}$ are not influenced by the reaction process and are to some extent apparatus constants, $$q_{Re}=const-L+C_2{}^*dT_2/dt.$$

If q=0 (as in the present example), then $$L-const=C_2{}^*dT_2/dt,$$

i.e. in this case it is possible with the aid of L (sum of the thermal outputs) and the rate of change $dT_2/dt$ of the temperature of the measuring cell 2 to determine the effective heat capacity $C_2$ of the measuring cell content.

In the present example, the temperature $T_2$ varied sinusoidally by a constant value with the amplitude $\Delta T$ and the angular frequency w. The following therefore applied $$L-const=\Delta L=C_2{}^*\Delta T^*w^*\cos(w^*t).$$

i.e. from the maximum fluctuation $\Delta L_o$ of the sum of the thermal outputs (FIG. 6) and the maximum amplitude of the temperature fluctuation $\Delta T$, the effective heat capacity $C_2$ was calculated using $$C_2=\Delta L_o/(\Delta T^*w).$$

The result was $C_2=2472$ J/degree.

As expected, $C_2$ is greater than the heat capacity of the pure silicone oil content, because the effective heat capacity of the measuring cell content is made up both of the heat capacity of the silicone oil (2081 J/degree) and of the heat capacities of the agitator 4, power breakers and a fraction of the measuring cell wall.

To simulate a heat output rate of a reaction, an electric heating element was installed in the measuring cell. FIG. 7 shows the time characteristic of the heat output rate $q_{Re}$ generated by the heating element (smooth line) and the compensating characteristic of the thermal output $L=L_1+L_2+q_{Rü2}$ of the calorimeter sensor (fluctuating line). The temperature of the production reactor was constant during measurement. For recording purposes, the signals for $q_{Re}$ (simulation heating) and L were recorded with opposite signs by a recording instrument and, prior to the start of the simulated reaction, were brought into coincidence by shifting their points of origin. Even after setting in of the "reaction" ($q_{Re}\approx o$), the time characteristic of both lines must agree under the given conditions (see FIG. 7).

We claim:

1. A process for measuring the heat output rate in a reactor (3) with the aid of a calorimeter, which comprises a measuring cell (2), an intermediate thermostat (1) and a base thermostat (0), and taking as a basis the heat balance equation of the measuring cell (2)

$$q_{Re} + q_{Mi} + q_{Rü2} + L_2 + m \cdot c_3 \cdot T_3 - m \cdot c_2 \cdot T_2 = C_2 \cdot dT_2/dt + KF_{21} \cdot (T_2 - T_1),$$

with the quantity $KF_{21} \cdot (T_2 - T_1)$ being determined using the heat balance equation of the intermediate thermostat (1)

$$KF_{21} \cdot (T_2 - T_1) + L_{Rü1} + L_1 = KF_{10} \cdot (T_1 - T_0).$$

in which $C_2$ = effective heat capacity of the measuring cell content,
$q_{Re}$ = heat output rate as a result of reaction in the measuring cell,
$q_{Mi}$ = heat output rate as a result of mixing in the measuring cell,
$q_{Rü2}$ = heat output rate as a result of agitation in the measuring cell,
$L_2$ = electrical heat output in the measuring cell,
m = mass flow through the measuring cell,
$c_3$ = specific heat of the inflow mass (production reactor),
$c_2$ = specific heat of the outflow mass (measuring cell),
$T_3$ = temperature of the production reactor,
$T_2$ = temperature of the measuring cell,
$T_1$ = temperature of the intermediate thermostat, and
$KF_{21}$ = diathermancy of the measuring cell to the intermediate thermostat; said process comprising the steps of:

continuously adjusting the composition of the substance in the measuring cell (2) of the calorimeter to be the same as the composition of the substance in the reactor (3) ($q_{mi} = 0$ and $c_2 = c_3$);

continuously adjusting the temperature of the substance in the measuring cell (2) to be the same as the temperature of the substance in the reactor (3) ($m \cdot c_3 \cdot T_2 - m \cdot c_2 \cdot T_2 = 0$);

interrupting the transport of substance from the reactor (3) into the measuring cell (2) for a period $\delta t$;

during said period $\delta t$ determining the effective heat capacity $C_2$, taking as a basis the then prevailing heat balance equation $$C_2 \cdot dT_2/dt = q_{Re} + q_{Rü2} - KF_{21} \cdot (T_2 - T_1);$$

determining the heat output rate $q_{Re}$ of the measuring cell (2) from the heat balance of the measuring cell (2); and determining the heat output rate in the reactor (3), taking into account at least one of the volume or mass ratio between the reactor and measuring cell contents.

2. The process according to claim 1, wherein the effective heat capacity $C_2$ is determined in the period $\delta t$ by the steps of measuring $T_2$ and $T_1$, assuming $C_2$ itself and $KF_{21}$ are constant, and replacing $q_{Re} + q_{Rü2}$ for the period $\delta t$ by a mean heat output rate $q_m$.

3. The process according to claim 1, wherein the effective heat capacity $C_2$ is determined by the steps of measuring $T_1$ and $T_2$ during the period $\delta t$ and determining the unknown parameters $C_2$ and $q_{Re}$ in the heat balance equation $$C_2 \cdot dT_2/dt = q_{Re} + q_{Rü2} - KF_{21} \cdot (T_2 - T_1)$$

by carrying out a known mathematical method.

4. The process according to claim 1, wherein the temperature of the substance mixture upon entry into the measuring cell (2) is kept equal to the temperature of the substance in the reactor (3) by heating or cooling the connecting line (12) between the reactor (3) and the measuring cell (2).

5. In a calorimeter for measuring the heat output rate of a reactor, said calorimeter comprising a measuring cell (2), which has at least one temperature detector (6), a controllable heating device (5) with an output measuring circuit (7) and an agitator (4), an intermediate thermostat (1), which has at least one temperature detector (9) and a controllable heating device (11) with an output measuring circuit (17), and a base thermostat (0), with the controllable heating device (11) maintaining a constant temperature difference $T_1$ between the base and the intermediate thermostat (0,1), the improvement wherein the calorimeter further comprises at least one connection (12) for transporting a substance from the reactor (3) into the measuring cell (2) of the calorimeter and a measurement and control unit (7) which adjusts the temperature in the measuring cell (2) to the temperature in the reactor (3).

6. The calorimeter according to claim 5, wherein the connection (12) has a pump device (13) for circulating a substance between the reactor (3) and the measuring cell (2).

7. The calorimeter according to claim 5, wherein the inlet point of the connection (12) into the measuring cell (2) has a temperature detector (15) and the connection (12) has a controllable heating/cooling device (16) with a control unit (17) which adjusts the inlet temperature of the substance mixture coming from the reactor (3) into the measuring cell (2) to the temperature prevailing in the reactor (3).

* * * * *